United States Patent [19]

Casida et al.

[11] Patent Number: 4,942,173
[45] Date of Patent: Jul. 17, 1990

[54] PESTICIDAL COMPOUNDS

[75] Inventors: John E. Casida, Berkeley, Calif.; Christopher J. Palmer, Ipswich; John P. Larkin, Buzzard, both of England; Ian H. Smith, Eaton Bray, United Kingdom

[73] Assignee: The Regents of the University of California, Berkeley, Calif.

[21] Appl. No.: 315,247

[22] Filed: Feb. 24, 1989

Related U.S. Application Data

[63] Continuation of Ser. No. 891,697, Jul. 29, 1986, abandoned, Continuation-in-part of Ser. No. 779,167, Sep. 23, 1985, Pat. No. 4,772,624, which is a continuation-in-part of Ser. No. 692,818, Jan. 23, 1984, which is a continuation-in-part of Ser. No. 575,843, Jan. 30, 1984.

[30] Foreign Application Priority Data

Mar. 12, 1986 [GB] United Kingdom ............... 8606130

[51] Int. Cl.$^5$ .................... C07D 323/04; A01N 43/32
[52] U.S. Cl. .................... 514/452; 549/214; 549/336; 549/363
[58] Field of Search .............. 549/214, 336, 363; 514/452

[56] References Cited

U.S. PATENT DOCUMENTS

| 3,577,438 | 5/1971 | Melaas ........................... 549/363 |
| 3,686,224 | 8/1972 | Deffner ........................... 549/363 |
| 4,772,624 | 9/1988 | Palmer et al. ..................... 514/452 |

FOREIGN PATENT DOCUMENTS 0059985 4/1983 Japan ........................... 549/363

OTHER PUBLICATIONS

Nishida, H. et al., "Alkyd Resin Adhesives", CA 104 208533 z.

Primary Examiner—Mukund J. Shah
Assistant Examiner—C. L. Cseh
Attorney, Agent, or Firm—Nixon & Vanderhye

[57] ABSTRACT

The present invention relates to a compound of the formula (I):

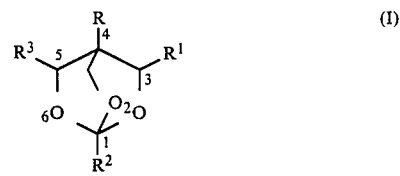

wherein R is $C_{2-10}$ alkyl, alkenyl or alkynyl, each optionally substituted by or methyl substituted by cyano, $C_{3-4}$ cycloalkyl, halo, $C_{1-4}$ alkoxy or a group $S(O)_m R^4$ where $R^4$ is $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)_m R^4$ as defined hereinbefore; $R^1$ is halo, $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms, a group $S(O)_m R^4$ as defined hereinbefore or alkynyl substituted by tri-$C_{1-4}$ alkylsilyl, or $R^1$ is cyano, spiro-cyclopropyl, gem dimethyl, gem dicyano, gem diethynyl, oxo or methylene optionally substituted by cyano of $C_{1-3}$ alkyl optionally substituted by fluorine, or $R^1$ and R and the carbon atoms to which they are attached form a $C_{5-7}$ carbocyclic ring optionally substituted by halo, $C_{1-3}$ alkyl or alkoxy or $C_{2-3}$ alkenyl, $R^2$ is phenyl substituted by an $C_{2-3}$ alkynyl group or by a tri-$C_{1-4}$ alkylsilylalkynyl group and $R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo, or $R^3$ is cyano or halo, its use in medicine, pharmaceutical compositions containing it and its preparation.

9 Claims, No Drawings

PESTICIDAL COMPOUNDS

This invention was made with Government support under Grant No. ES00049 awarded by the Department of Health and Human Services. The Government has certain rights in this invention.

This is a continuation of application Ser. No. 06/891,697, filed July 29, 1986, now abandoned, which is a continuation-in-part of co-pending application Ser. No. 779,167, filed Sept. 23, 1985 which is in turn a continuation-in-part application of Ser. No. 692,818, filed Jan. 23, 1984 which is in turn a continuation-in-part application of Ser. No. 575,843, filed Jan. 30, 1984.

The present invention relates to novel chemical compounds having pesticidal activity, to methods for their preparation, to compositions containing them and to their use in the control of pests. More particularly the invention relates to a class of 1,3,4-tri-substituted-2,6,7-trioxabicyclo[2,2,2]octanes.

The use of certain 2,6,7-trioxabicyclo[2,2,2]octanes as pesticides is disclosed in European Patent Application No. 152 229; it has now been discovered that derivatives of these compounds having substituents at the 3-position have interesting pesticidal activity.

Accordingly the present invention provides a compound of the formula (I):

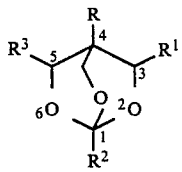

wherein R is $C_{2-10}$ alkyl, alkenyl or alkynyl, each optionally substituted by or methyl substituted by cyano, $C_{3-4}$ cycloalkyl, halo, $C_{1-4}$ alkoxy or a group $S(O)m\ R^4$ where $R^4$ is $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)m\ R^4$ as defined hereinbefore; $R^1$ is halo, $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms, a group $S(O)m\ R^4$ as defined hereinbefore or alkynyl substituted by tri-$C_{1-4}$ alkylsilyl, or $R^1$ is cyano, spiro-cyclopropyl, gem dimethyl, gem dicyano, gem diethynyl, oxo or methylene optionally substituted by cyano or $C_{1-3}$ alkyl optionally substituted by fluorine, or $R^1$ and R and the carbon atoms to which they are attached form a $C_{5-7}$ carbocyclic ring optionally substituted by halo, $C_{1-3}$ alkyl or alkoxy or $C_{2-3}$ alkenyl, $R^2$ is phenyl substituted by an $C_{2-3}$ alkynyl group or by a tri-$C_{1-4}$ alkylsilylalkynyl group and $R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo, or $R^3$ is cyano or halo.

Suitably R is propyl, butyl, pentyl, $C_{2-5}$ alkenyl or alkynyl, $C_{5-7}$ cycloalkyl or phenyl each optionally substituted by one to three fluoro, chloro or bromo. Most suitably R is n-propyl, n-butyl, i-butyl, s-butyl, t-butyl, cyclopentyl or cyclohexyl and preferably R is n-propyl, n-butyl, i-butyl, t-butyl or cyclohexyl.

Suitably $R^1$ is cyano, ethynyl or methyl or ethyl optionally substituted by cyano, methoxy, methylthio or fluoro. Most suitably $R^1$ is methyl, cyano, ethynyl, trifluoromethyl or ethyl. Preferably $R^1$ is methyl, trifluoromethyl, cyano or ethynyl.

Additionally suitable substituents for the substituted phenyl group, $R^2$, include halo, cyano, azido, tetrazolyl, a group $SO_2R^5$ wherein $R^5$ is amino or di-$C_{1-4}$ alkylamino, a group $COR^6$ wherein $R^6$ is $C_{1-4}$ alkoxy, benzyloxy, amino or di-$C_{1-4}$ alkylamino, nitro, $C_{1-3}$ alkyl optionally substituted by halo, cyano or ethynyl, or $C_{2-3}$ alkenyl optionally substituted by halo or tri-$C_{1-4}$ alkylsilyl. When $R^2$ is phenyl, $C_{5-10}$ cycloalkyl or cycloalkenyl substituted by an acidic or basic group, salts can be formed of compounds of the formula (I). The present invention includes salts of the compounds of formula (I). The preparation of such salts is carried out by methods well known to those skilled in the art. Typical salts include acid addition salts, such as those from mineral acids, and basic salts, such as those from the alkali earth metals.

Suitably the alkynyl group is at the 3-, 4- or 5-position of the phenyl ring. If other substituents are present these are suitably halo, cyano, azido or nitro at the 3-, 4- and/or 5-position and/or fluoro at the 2- and/or 6-position. Most suitably $R^2$ is phenyl substituted at the 3-, 4- and/or 5-position by ethynyl and optionally by chloro, bromo, iodo, or cyano. Preferably $R^2$ is phenyl substituted at the 4-position by ethynyl.

Suitably $R^3$ is hydrogen or methyl.
Preferably $R^3$ is hydrogen

Suitable compounds of the formula (I) include those of the formula (IA)

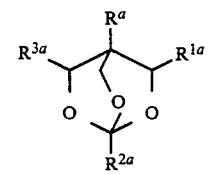

wherein $R^a$ is $C_{2-4}$ alkyl, alkenyl or alkynyl, $C_{5-10}$ cycloalkyl or phenyl, each optionally substituted by cyano or $C_{1-4}$ alkoxy, $R^{1a}$ is cyano or $C_{1-3}$ alkyl, $C_{2-3}$ alkenyl or alkynyl each optionally substituted by cyano, $C_{1-4}$ alkoxy, $C_{1-4}$ alkylthio or halo, or $R^{1a}$ is cyano, gem dimethyl or $R^{1a}$ and $R^a$ and the carbon atoms to which they are attached form a $C_{5-7}$ carbocyclic ring optionally substituted by $C_{1-3}$ alkyl or alkoxy; $R^{2a}$ is phenyl substituted by an $C_{2-3}$ alkynyl group and $R^{3a}$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo.

Suitably $R^a$ is propyl, butyl, $C_{5-7}$ cycloalkyl or phenyl. Most suitably $R^1$ is n-propyl, butyl, cyclopentyl or cyclohexyl and preferably $R^a$ is propyl, butyl or cyclohexyl.

Suitably $R^{1a}$ is cyano, methyl or ethyl optionally substituted by cyano, methoxy, methylthio or fluoro. Preferably $R^{1a}$ is methyl or ethyl.

Suitable substituents for $R^{2a}$ other than alkynyl include halo, cyano, azido, nitro, $C_{1-3}$ alkyl optionally substituted by halo or $C_{2-3}$ alkenyl optionally substituted by halo.

Preferred compounds of the present invention include
1-(4-ethynylphenyl)-3-methyl-4-n-propyl-2,6,7-trioxabicyclo[2,2,2]octane
3-methyl-4-n-propyl-1-[4-(2-trimethylsilylethynyl)-phenyl]-2,6,7-trioxabicyclo[2,2,2]octane 1-(4-ethynylphenyl)-4-n-propyl-3-trifluoromethyl-2,6,7-trioxabicyclo[2,2,2]octane 4-n-propyl-3-trifluoromethyl-1-[4-(2-trimethylsilylethynyl)-phenyl]-2,6,7-trioxabicyclo[2,2,2]octane 3-cyano-1-(4-ethynylphenyl)-4-n-propyl-2,6,7-trioxabicyclo[2,2,2]octane 4-t-butyl-3-cyano-1-[4-(2-trimethylsilylethynyl)-phenyl]-2,6,7-trioxabicyclo[2,2,2]octane 4-t-butyl-3-cyano-1-(4-ethynylphenyl)-2,6,7-trioxabicyclo[2,2,2]octane The compounds of the formula (I) may be prepared from the corresponding iodophenyl compound (i.e. a compound of formula (I) in which $R^2$ is iodo) via the corresponding tri-$C_{1-4}$alkylsilylalkynylphenyl intermediate. The trialkylsilylalkynylphenyl intermediates which have useful pesticidal activity in their own right may be formed by the reaction of the iodo compound with a trialkylsilylalkyne conveniently in the presence of a cuprous salt, such as cuprous iodide, and bis-triphenylphosphine palladium dichloride in a base, such as diethylamine, at a non-extreme temperature, for example at room temperature. The silyl intermediate may then be converted to the compound of formula (I) by methods well known to those skilled in the art, for example by reaction with tetrabutyl-ammonium fluoride in an ether, such as tetrahydrofuran, at a non-extreme temperature, conveniently room temperature.

The process for the preparation of a compound of the formula (I) wherein $R^2$ is phenyl substituted by iodo may be any method known in the art for preparing analogous compounds, for example by the condensation of a triol of the formula (II) with an orthocarboxylate of the formula $R^{2x}C(OR^7)_3$.

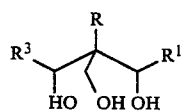
(II)

wherein $R^1$ and $R^3$ are as hereinbefore defined, $R^{2x}$ is phenyl substituted by iodo and $R^7$ is $C_{1-4}$ alkyl, phenyl or $C_{7-8}$ aralkyl. Suitably $R^4$ is methyl or ethyl, preferably methyl. The reaction is normally carried out in the presence of an acid such as a mineral acid conveniently hydrochloric acid, or a sulphonic acid derivative, such as toluene sulphonic acid, or an acid resin, or in the presence of a trialkyl amine, such as triethylamine, at an elevated temperature, for example between 50° and 200° C., conveniently between 120° and 170° C. The reaction may conveniently be carried out in the absence of a solvent but a suitable solvent may be added if desired.

The triol of the formula (II) may be prepared:

(i) from the corresponding triol where $R^1$ and/or $R^3$ are hydrogen via a protected aldehyde which is reacted with a reagent, such as a Grignard reagent, which is suitable for lengthening the carbon chain followed by deprotection, i.e. as represented in Scheme 1. In certain cases, it may be convenient to prepare triol derivatives where $R^1$, $R^3$ are hydrogen and one of the hydroxy groups is protected, by reduction of an ester of the formula (III):

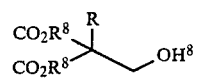

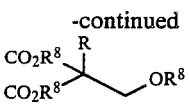
(III)

wherein $R^8$ is a protecting group such as benzyl and $R^9$ is $C_{1-4}$ alkyl. This reduction is suitably carried out by a complex hydride such as lithium aluminium hydride in an inert solvent conveniently an ether. The compound of the formula (III) may be prepared from the corresponding compound RCH $(CO_2R^9)_2$ by reaction with a compound $XCH_2OR^8$, wherein X is a leaving group such as a halogen, in the presence of a strong base, such as sodium hydride.

(ii) when it is required to prepare a compound of the formula (I) wherein $R^3$ is hydrogen, by the reduction of a compound of the formula (IV):

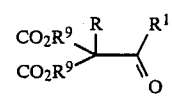
(IV)

wherein R, $R^1$ and $R^9$ are as hereinbefore defined. This reduction is suitably carried out by means of a complex hydride, such as lithium aluminium hydride in an inert solvent such as an ether, for example diethyl ether.

When R and $R^1$ are linked to form a carbocyclic ring, the compound of the formula (IV) is conveniently prepared by the reaction of a compound of the formula (V)

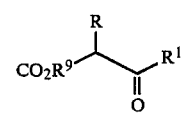
(V)

with a compound hal $CO_2R^9$, wherein R, $R^1$, and $R^9$ are as hereinbefore defined and hal is halogen, for example chlorine. This reaction is conveniently carried out in the presence of a Grignard reagent for example ethyl magnesium bromide, in an inert solvent such as an ether, for example tetrahydrofuran. Other compounds of the formula (IV) are conveniently prepared by the reaction of a compound RCH $(CO_2R^9)_2$ with a compound hal $CO.R^1$ wherein R, $R^1$, $R^9$ and hal are as hereinbefore defined in a trifluoroacylating agent such as trifluoroacetic anhydridetrifluoroacetic acid or ethyl trifluoroacetate. This reaction is conveniently carried out in the presence of a strong base, such as a metal hydride in a non-polar solvent, for example an aromatic hydrocarbon such as benzene or toluene.

The compounds of the formula (I) wherein $R^2$ is a group $R^{2a}$ may also be prepared by the cyclisation of a compound of the formula (VI)

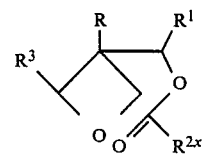
(VI)

wherein R to $R^3$ are as hereinbefore defined in the presence of an acid catalyst. Boron trifluoride etherate is a particularly preferred acid catalyst for this cyclisation which will normally be carried out in an inert solvent, such as a halogenated hydrocarbon, conveniently dichloromethane, at below ambient temperature, for example between $-100°$ and $0°$ C. and conveniently between $-70°$ and $-50°$ C.

The compounds of the formula (VI) may be prepared by the reaction of compounds of the formula (VII) and (VIII):

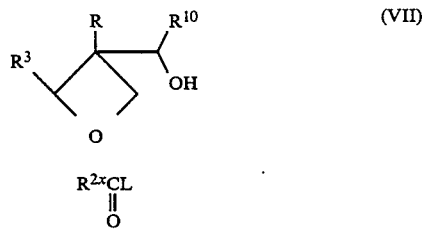

where $R^{10}$ is a group $R^1$ and R to $R^3$ are as hereinbefore defined and L is leaving group such as halo. This reaction conveniently takes place in an inert solvent in the presence of base at a non-extreme temperature. Halogenated hydrocarbons, such as dichloromethane are particularly suitable solvents, pyridine is a preferred base and the reaction will conveniently be carried out at between $-50°$ and $100°$ C., preferably at $0°$ C.

The compounds of the formula (VII) may in turn be prepared from compounds of the formula (II) by reaction with diethyl carbonate in the presence of a strong base, for example potassium hydroxide, in a polar solvent, such as an alcohol, for example ethanol, at an elevated temperature, for example between $50°$ and $100°$ C. This is a preferred method of making compounds of the formula (VII) wherein $R^1=R^{10}=CF_3$.

The compounds of the formula (VII) may alternatively be prepared by the reaction of a Grignard reagent $R^1$ Mg Hal or an $C_{2-4}$ alkynyl lithium compound or sodium cyanide with a compound of the formula (IX)

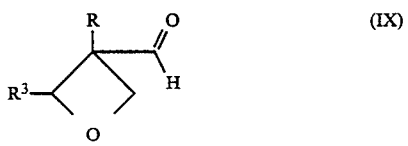

wherein R, $R^1$ and $R^3$ are as hereinbefore defined and Hal is a halogen atom such as bromine or iodine. This reaction is conveniently carried out in an inert solvent, suitably an ether for example diethyl ether or dioxane at a non-extreme temperature, for example between $-50°$ and $50°$ C. and preferably between $-10°$ and $10°$ C. The alkynyl lithium compound is conveniently present as a complex, for example with ethylenedianime. The sodium cyanide is conveniently added as an aqueous solution. The compounds of the formula (IX) may be prepared by oxidation of compounds of the formula (VII) wherein $R^{10}$ is hydrogen by using oxalyl chloride and dimethyl sulphoxide in an inert solvent, such as a halogenated hydrocarbon, for example dichloromethane, followed by a base such as triethylamine or by using pyridinium chlorochromate in an inert solvent, such as a halogenated hydrocarbon, for example dichloromethane.

The compounds of the formula (VII) wherein $R^{10}$ is hydrogen may be prepared in an analogous manner from compounds of formula (II) to the preparation of the compounds of the formula (VII) where $R^{10}$ is trifluoromethyl.

One compound of the formula (I) may be converted to another compound of the formula (I) by methods well known to those skilled in the art.

The compounds of Formula (I) may be used to control arthropods such as insect and acarine pests. Thus in a further aspect, the, present invention provides a method of controlling arthropods on animals which comprises the administration of an arthopodially effective amount of a compound of the formula (I) to the animal.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising emanator such as a vapourising mat, wettable powder, granule, aerosol, emulsifiable concentrate, oil suspensions, oil solutions, impregnated article or pour on formulation. Dip concentrates are not applied per se, but diluted with water and the animals immersed in a dipping bath containing the dip wash. Sprays may be applied by hand or by means of a spray race or arch or by means of space spraying machinery. The animal; plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals, plants or surface, as space sprays or aerosols, or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, silicone dioxide, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 1 to 90% w/v of the composition and may be selected from kerosene, ketones, alcohols, xylene, aromatic naphtha, aromatic and aliphatic esters and other solvents known in the formulating art. The concentration of emulsifiers may be varied within wide limits but is preferably in the range of 0.5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Wettable powders and emulsifiable concentrates will normally contain from 1 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispensing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body.

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formations such as pour-on formulations which in general will be deposited at a concentration in the range from 0.1 to 20.0% and preferably 0.1 to 10%.

The compounds of formula (I) are also of use in the protection and treatment of plant species, in which case an effective insecticidal or acaricidal amount of the active ingredient is applied. The application rate will vary according to the compound chosen, the nature of the formulation, the mode of application, the plant species, the planting density and likely infestation and other like factors but in general, a suitable use rate for agricultural crops in the range 0.001 to 3 Kg/Ha and preferably between 0.01 and 1 Kg/Ha. Typical formulations for agricultural use contain between 0.0001% and 50% of a compound of formula (I) and conveniently between 0.1 and 15% by weight of a compound of the formula (I).

Particular crops include cotton, wheat, maize, rice, sorghum, soya, vines, tomatoes, potatoes, fruit trees and spruce.

Dusts, greases, pastes, surface and space sprays and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, compounds of formula (I) have activity against other arthropod pest including *Tetranychus urticae, Plutella xylostella,* Culex spp. and *Blattella germanica*. The compounds of formula (I) are thus useful in the control of arthropods e.g. insects and acarines in any environment where these constitute pests, e.g. in agriculture, in animal husbandry, in public health and in domestic situations.

Insect pests include members of the order Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma, Liriomyza and Melophagus spp.), Phthiraptera (Malophaga e.g. Damalina spp. and Anoplura e.g. Pediculus humanus capitis, Pediculus humanus, humanus, Phythirus pubis Linognathus and Haematopinus spp.), Hemiptera (e.g. Aphis, Bemisia, Aleurodes, Nilopavata, Nephrotetix or Cimex spp.), Orthoptera (e.g. Schistocerca or Acheta spp.), Dictyoptera (e.g. Blattela, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.) and Pscoptera (e.g. Peripsocus spp.).

Acarine pest include ticks, e.g. members of the genera Boophilus, Rhipicephalus, Amblyomma, Hyalomma, Ixodes, Haemaphysalis, Dermocentor and Anocentor, and mites and manges such as Sarcoptes scabiei, and Tetranychus, Psoroptes, Notoedres, Psorergates, Chorioptes and Demodex spp.

Compounds of the invention may be combined with one or more other active ingredient (for example pyrethroids, carbamates and organophosphates) and/or with attractants and/or with fungicides and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1-1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:
(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of arthropod pests, such as insect or acarine pests comprising the application to the pest or its environment of a compound of Formula (I);
(f) synergised pesticidal compositions comprising a compound of Formula (I); and
(g) potentiating or non-potentiating mixtures of a compound of Formula (I) and another pesticidal compound;
(h) novel intermediates of the preparation of compounds of Formula (I).

The following Examples illustrate, in a non-limiting manner, preferred aspects of the invention.

The physical data for each of the compounds of the formula (I) is provided in tables after the examples. All indicated temperatures are in °Celsius.

EXAMPLE A 1-(4-ethynylphenyl)-3-methyl-4-n-propyl-2,6,7-trioxabicyclo[2,2,2]octane.

(i) A mixture of 3,3-di(hydroxymethyl)-1,1,1-trifluorohexan-2-ol (2.8 g.), diethyl carbonate (1.6 ml.), potassium hydroxide (0.1 g) and dry ethanol (4.0 mls) was refluxed gently (oil bath 110°), under a current of nitrogen, for 30 minutes. The ethanol was then removed by distillation. Distillation gave 3-(1-hydroxy-2,2,2-trifluoroethyl)-3-n-propyloxethane (1.7 g.), a colourless oil (b.p. 112°, 20-25 m.m.).

Gas-liquid chromatography (g.l.c.): OV 210 at 120° produced one peak.

Infrared spectrum (IR) (liquid film): 3450 (s,br), 1300 (s), 1170 (s), 1130 (s), 1045 (s).

(ii) A solution of 4-iodobenzoyl chloride (2.1 g.) in dry dichloromethane (25 mls) was added to a stirred solution of 3-(1-hydroxy-2,2,2-trifluoroethyl)-3-n-propyl-oxetane (1.55 g.) and pyridine (1.0 ml.) in dry dichloromethane, at 0°. The reaction mixture was stirred for 24 hours, at room temperature. The mixture was poured into water and the aqueous mixture was extracted with diethyl ether. The ethereal extracts were washed with water, dried over anhydrous magnesium sulphate and evaporated in vacuo. The residue was purified by column chromatography on silica, eluting with 1% triethylamine in hexane.

3-[1-(4-Iodobenzoyloxy)-2,2,2-trifluoroethyl]-3-n-propyloxetane was obtained as a colourless oil (2.4 g.).

Gas-liquid chromatography (g.l.c.): OV 210 at 200° produced one peak.

Nuclear magnetic resonance spectrum (NMR) was follows: $^1$H (ppm from TMS in CDCl$_3$, integral, number of peaks): 7.70, 4H, m; 4.80-4.20, 5H, m; 2.20-0.80, 7H, m.

(iii) Boron trifluoride etherate (0.54 ml.) was added to a stirred solution of 3-[1-(4-iodobenzoyloxy)-2,2,2-trifluoroethyl]-3-n-propyloxetane (2.3 g.) in dry dichloromethane (50 mls.) at −70°. The mixture was allowed to warm up slowly to room temperature and was then stirred for 12 hours. Triethylamine (1.0 ml.) was added and the mixture was poured into water. The aqueous mixture was extracted with diethyl ether. The ethereal extracts were washed with water, dried over anhydrous magnesium sulphate and evaporated in vacuo. The residue was purified by column chromatography on alumina eluting with 1:4 dichloromethane:hexane saturated with ammonia.

1-(4-Iodophenyl)-4-n-propyl-3-trifluoromethyl-2,6,7-trioxabicyclo(2,2,2)octane was obtained as a colourless solid (0.53 g.).

Gas-liquid chromatography (g.l.c.): OV 210 at 220° produced one peak.

Nuclear magnetic resonance spectrum (N.M.R.) was as follows: $^1$H (ppm from TMS is CDCl$_3$, integral, number of peaks, J$_{Hz}$): 7.70, 2H, d, 8; 7.30, 2H, d, 8; 4.80-3.80, 5H, m; 1.40, 4H, m; 1.00, 3H, m.

(iv) Bis-triphenylphosphine palladium dichloride (20 mg.) and cuprous iodide (5 mg.) were added to a stirred solution of 1-(4-iodophenyl)-4-n-propyl-3-trifluoromethyl-2,6,7-trioxabicyclo[2,2,2]octane (0.5 g) and trimethylsilylacetylene (0.24 ml.) in dry diethylamine (20 mls.). The mixture was stirred at room temperature for 12 hours. The mixture was evaporated in vacuo. and the residue was dissolved in diethyl ether. The ethereal solution was washed with water, dried over anhydrous magnesium sulphate and evaporated in vacuo. The residue was purified by column chromatography on alumina eluting with 1:4 dichloromethane:hexane, saturated with ammonia. 4-n-Propyl-3-trifluoromethyl-1-[1-[4-(2-trimethylsilylethynyl)phenyl]-2,6,7-trioxabicyclo[2,2,2]octane was obtained as a pale brown solid (0.36 g.).

Gas-liquid chromatography (g.l.c.): OV 210 at 230° produced one peak.

(v) Tetrabutylammonium fluoride solution (0.84 ml., 1M solution in tetrahydrofuran) was added to a stirred solution of 4-n-propyl-3-trifluoromethyl-1-[4-(2-trimethylsilylethynyl)phenyl]-2,6,7-trioxabicyclo[2,2,2]octane (0.28 g.) in dry tetrahydrofuran (5 mls). The mixture was stirred for 30 minutes at room temperature. The solvent was removed in vacuo and the residue was dissolved in dry diethyl ether. The ethereal solution was washed with water, dried over anhydrous magnesium sulphate and evaporated in vacuo. The residue was recrystallised from hexane. 1-(4-Ethynylphenyl)-4-n-propyl-3-trifluoromethyl-2,6,7-trioxabicyclo[2,2,2]octane was obtained as a pale yellow solid (70 mg.).

Gas-liquid chromatography (g.l.c.): OV 210 at 230° produced one peak.

EXAMPLE B

1-(4-Ethynylphenyl)-3-Methyl-4Propyl-2,6,7-Trioxabicyclo[2,2,2]Octane.

(i) A mixture of 2,2-di-(hydroxymethyl)pentan-1-ol (24.6 g), diethyl carbonate (20.1 ml.), potassium hydroxide (0.3 g.) and dry ethanol (2 ml) was heated to gentle reflux (oil bath 110°–120°) under a stream of nitrogen for 30 minutes. After this time the ethanol formed was removed by distillation at atmospheric pressure (oil bath 130°–140°, still head temperature 76°). The pressure was reduced to 20 mm. Hg and the oil bath temperature adjusted to 230°. 3-hydroxymethyl-3-n-propyl oxetane distilled as a colourless liquid (16.7 gms, head temperature 120°–126°).

Gas-liquid chromatography (g.l.c.): OV-210 at 120° produced one peak. Nuclear magnetic resonance spectrum (N.M.R.) was as follows: $^1$H (ppm from TMS in CDCl$_3$, integral, multiplicity): 4.35, 4H, s; 3.60, 2H, m; 1.8–0.7, 7H, m.

(ii) A solution on dimethyl sulphoxide (12 ml) in dry dichloromethane (4.0 ml.) was added to a solution of oxalyl chloride (7.4 ml) in dichloromethane (25 ml) stirred at −70° under nitrogen. After the addition was complete the resulting mixture was stirred for a further 5 minutes at −70° before a solution of 3-hydroxymethyl-3-n-propyloxetane (10.0 g) in dichloromethane (25 ml) was added, dropwise, over 10 minutes. The resulting mixture was allowed to stir for a further 30 minutes when neat triethylamine (54 ml) was added over approximately 30 minutes. The reaction mixture was allowed to warm to room temperature over 3 hours when it was poured into water. The organic phase was separated and the aqueous layer further extracted with fresh dichloromethane. The combined organic extracts were washed with dilute hydrochloric acid, saturated sodium bicarbonate and brine. The resulting organic phase was dried over anhydrous magnesium sulphate and evaporated in vacuo to give 3-formyl-3-n-propyloxetane (10.5 g) as a yellow oil.

Gas-liquid chromatography (g.l.c.): OV-210 at 120° produced one peak.

Infrared spectrum (IR) (liquid film): 1730 cm$^{-1}$.

Nuclear magnetic resonance spectrum (N.M.R.) was as follows: $^1$H (ppm from TMS in CDCl$_3$, integral, multiplicity, JH$_z$): 9.0, iH, S; 4.90, 2H, d, 6; 4.60, 2H, d, 6; 2.30–1.0, 7H, m.

(iii) A solution of 3-formyl-3-n-propyloxethane (10 g) in dry ether (50 ml) was added to a stirred solution of methyl magnesium iodide (0.078 moles) in ether (100 ml) at 0° C. under nitrogen. The reaction mixture was allowed to warm to room temperature and stirred for a further 3 hours. After this time it was cooled to 0° C. and sufficient saturated ammonium chloride solution was added slowly to dissolve the resulting precipitate. The organic phase was separated and the aqueous layer re-extracted with fresh ether. The combined organic extracts were washed with brine, dried over anhydrous magnesium sulphate and then evaporated in vacuo. The residue was purified by column chromatography on silica, gradient elution with hexane/ether mixtures. Elution with neat ether gave 3-(1-hydroxyethyl)-3-n-propyl oxetane as an oil (2.5 g).

Gas-liquid chromatography (g.l.c.): OV-210 at 120° produced one peak.

Infrared spectrum (IR) (liquid film): 3420 (s,br), 1470 (s), 1120 (s), 985 (s) cm$^{-1}$.

Nuclear magnetic resonance spectrum (N.M.R.) was as follows: $^1$H (ppm from TMS in CDCl$_3$, integral, multiplicity, JH$_z$): 4.65, 2H, d, 6; 4.35, 2H, d, 6; 3.9, 1H, q 6; 1.15, 3H, d, 6; 1.9–0.8, 7H, m.

(iv) A solution of 4-iodobenzoyl chloride (3.5 g) in dry ether (25 ml) was added to a stirred solution of 3-(1-hydroxyethyl)-3-n-propyloxetane (1.7 g) and pyridine (1.8 ml) in ether (50 ml) at 0° C. The resulting mixture was stirred for 24 hours at room temperature. After this time the mixture was washed with water and brine. The organic extracts were dried over anhydrous magnesium sulphate and then evaporated in vacuo. The residue was purified by column chromatography on silica (pre-eluted with 1% triethylamine in hexane) and eluted with hexane/ether mixtures. 3-[1-(4-Iodobenzoyloxy)ethyl]-3-n-propyloxetane was obtained as a colourless oil (1.8 g).

Gas-liquid chromatography (g.l.c.): OV:210, programmed from 120° to 250° produced one peak.

Infrared spectrum (IR)(liquid film): 1730 (s), 1285 (s), 1115 (s), 1020 (s), 700 (s) cm$^{-1}$.

Nuclear magnetic resonance spectrum (N.M.R.) was follows: $^1$H (ppm from TMS in CDCl$_3$, integral, multiplicity) 7.8, 4H, s; 5.4, 1H, q; 4.85–4.35, 4H, m; 1.9–0.8, 10H, m.

(v) 3-[1-(4-Iodobenzoyloxy)ethyl]-3-n-propyloxetane was converted to 1-(4-ethynylphenyl)-3-methyl-4-propyl-2,6,7-trioxabicyclo[2,2,2]octane by a method strictly analogous to that described in example A steps (iii), (iv) and (v) and the corresponding intermediates isolated and characterised.

Gas liquid chromatography (g.l.c.) on the final product OV-17 at 240° C. produced one peak.

EXAMPLE C

4-t-Butyl-3-cyano-1-(4-ethynylphenyl)-2,6,7-trioxabicyclo[2,2,2]octane (i) To a stirred solution of pyridinium chlorochromate (6.5 g) in dry dichloromethane (50 ml), under a nitrogen atmosphere was added 3-t-butyl-3-hydroxymethyl-oxetane (2.9 g) in dichloromethane (10 ml). The mixture was stirred overnight and dry diethyl ether (100 ml) was added. The mixture was filtered through a column of fluorisil. The column was washed with further portions of ether (2×50 ml). The combined filtrates were evaporated in vacuo. 3-t-butyl-3-formyl-oxethane was obtained as a colourless solid (2.3 g).

Nuclear magnetic resonance spectrum (NMR) was as follows: $^1$H (ppm from TMS in CDCl$_3$, integral, number of peaks): 9.90, 1H, s; 4.70–4.40 (4H, q.); 1.05, 9H, s.

(ii) To a stirred solution of 3-t-butyl-3-formyl-oxetane (1.0 g) and 4-iodobenzoyl chloride (2.6 g) in dry diethyl ether (35 ml), under nitrogen, was added a solution of sodium cyanide (1.25 g) in water (1.0 ml). The mixture was stirred overnight. The mixture was poured into water (50 ml.) and the aqueous mixture was extracted with diethyl ether. The ethereal solution was dried over anhydrous sodium sulphate and then evaporated in vacuo. The residue was chromatographed on silica pre-treated with triethylamine eluting with hexane:chloroform 1:3. The 4-iodobenzoate of 3-t-butyl-3-(cyano-hydroxymethyl)-oxetane was obtained as a colourless solid (2.54 g.). Nuclear magnetic resonance spectrum (NMR) was as follows: $^1$H (ppm from TMS in CDCl$_3$, integral, number of peaks): 7.90–7.70, 4H, q; 5.80, 1H, s; 4.80–4.60, 4H, m; 1.10, 9H, s.

4-t-Butyl-3-cyano-1-[4-(2-trimethylsilylethynyl)-phenyl]-2,6,7-trioxabicyclo[2,2,2]octane was prepared from the 4-iodobenzoate of 3-t-butyl-3-(cyano-hydroxymethyl)oxetane using the methodology described in Example A.

A mixture of 4-t-butyl-3-cyano-1-[4-(2-trimethylsilylethynyl)-phenyl]-2,6,7-trioxabicyclo[2,2,2]octane (1.3 g.) and anhydrous potassium carbonate in dry methanol (125 ml.) was stirred under dry nitrogen for 2 hours. The resulting solution was evaporated in vacuo.

By analogous methods, the following compounds were also made:

7. 4-n-Butyl-3-methyl-1-[4-(2-trimethylsilylethynyl)-phenyl]-2,6,7-trioxabicyclo[2.2.2]octane.
8. 4-n-Butyl-1-(4-ethynylphenyl)-3-methyl-2,6,7-trioxabicyclo[2.2.2]octane.
9. 3-Cyano-4-n-propyl-1-[4-(2-trimethylsilylethynyl)-phenyl]-2,6,7-trioxabicyclo[2.2.2]octane.
10. 3-Cyano-1-(4-ethynylphenyl)-4-n-propyl-2,6,7-trioxabicyclo[2.2.2]octane.

| Number | $R^2$ | R | $R^1$ | m. pt. | Mass Spectrum Chemical Ionisation M + 1 | Infrared Spectrum |
|---|---|---|---|---|---|---|
| 1 | 4-Ethynyl-phenyl | nPr | $CF_3$ | solid | | 3310(w), 1172(s), 1130(m), 1115(m) |
| 2 | 4-[2-(trimethylsilyl)-ethynyl]-phenyl | nPr | $CF_3$ | solid | | |
| 3 | 4-ethynyl-phenyl | nPr | Me | solid | 273 | |
| 4 | 4-[2-(trimethylsilyl)-ethynyl]-phenyl | nPr | Me | solid | 345 | |
| 5 | 4-[2-trimethylsilyl)-ethynyl]-phenyl | t-Bu | CN | | | |
| 6 | 4-ethynyl-phenyl | t-Bu | CN | 123–125 | 298 | |
| 7 | 4-(2-trimethyl silyl-ethynyl) phenyl | n-Bu | Me | solid | 359 | |
| 8 | 4-ethynylphenyl | n-Bu | Me | solid | 287 | |
| 9 | 4-(2-trimethyl silyl-ethynyl)phenyl | n-Pr | CN | solid | | |
| 10 | 4-ethynylphenyl | n-Pr | CN | solid | | | t-Bu = tertiary butyl
n-Pr = normal propyl

| Number | Nuclear Magnetic Resonance Spectrum ($^1$H carried out in $CDCl_3$ and expressed as ppm from TMS, number of protons, number of peaks, $J_{Hz}$-(where appropriate)). |
|---|---|
| 1 | 7.40, 4H, m; 4.70–3.80, 5H, m; 3.05, 1H, s; 1.50–0.80, 7H, m. |
| 2 | 7.50, 4H, m; 4.80–3.90, 5H, m; 1.60–0.80, 7H, m; 0.40, 9H, s. |
| 3 | 7.40, 4H, m; 4.5–3.8, 5H, m; 3.0, 1H, s; 1.3, 3H, d, 6; 1.3–0.7, 7H, m. |
| 4 | 7.45, 4H, m; 4.4–3.9, 5H, m; 1.4, 3H, d, 6; 1.4–08, 7H, m, 0.3, 9H, s |
| 5 | 7.60–7.40, 4H, q; 4.95, 1H, d; 4.50–4.00, 4H, m; 1.00, 9H, s; 0.20, 9H, s. |
| 6 | 7.60–7.40, 4H, q; 4.95, 1H, d; 4.50–4.00, 4H, m; 3.05, 1H, s; 1.05, 9H, s. |
| 7 | 7.55, 2H, d, 7; 7.45, 2H, d, 7; 4.40–3.90, 5H, m; 1.40, 3H, d, 6; 1.30, 6H, m; 0.90, 3H, t, 6; 0.25, 9H, s. |
| 8 | 7.55, 2H, d, 7; 7.50, 2H, d, 7; 4.35, 1H, m; 4.25–3.95, 4H, m; 3.05, 1H, s; 1.50–1.10, 9H, m; 0.95, 3H, t, 7. |
| 9 | 7.50, 2H, d; 7.45, 2H, d; 4.90, 1H, d; 4.40–4.05, 4H, m; 1.50–1.10, 4H, m; 0.95, 3H, t; 0.20, 9H, s. |
| 10 | 7.50, 2H, d; 7.45, 2H, d; 4.95, 1H, d; 4.35–4.05, 4H, m; 3.05, 1H, s; 1.45–1.10, 4H, m; 0.95, 3H, t. |

The residue was taken up in diethyl ether and the ethereal solution was washed with water. The ethereal solution was dried over anhydrous sodium sulphate and evaporated in vacuo. The residue was purified by chromatography on alumina eluting with hexane:dichloromethane 4:1, saturated with ammonia. 4-t-butyl-3-cyano-1-(4-ethynylphenyl)-2,6,7-trioxabicyclo[2,2,2]octane was obtained as pale yellow needles (600 mg.).

From 3-formyl-3-isopropyl-oxetane and 4-cyanobenzoyl chloride and using the methodology described above, 3-cyano-1-(4-cyanophenyl)-4-isopropyl-2,6,7-trioxabicyclo[2,2,2]octane was prepared.

BIOLOGICAL ACTIVITY

The compound number refers to the numbers allocated to the compounds in the table spanning pages 22–23.

A. Lethal activity against House flies

The activity of compounds of the invention against unanaesthatised female *Musca domestica* (WRL strain), was demonstrated by the topical application to the test insect of a solution of the compound under test in butanone.

The activity of the test compound was also assessed when applied topically in conjunction with a synergist [6 μg piperonyl butoxide (PB) per insect]. Mortality was assessed after 24 and 48 hrs.

The following compounds were active at less than 1 μg/fly: 1,2,3,4.

B. Lethal Activity Against *Blattella germanica*

The activity of compounds of the invention against unanaesthatised male *Blatella germanica* (WRL strain), was demonstrated by the topical application to the test insect of a solution of the compound under test in butanone.

The activity of the test compound was also assessed when applied topically in conjunction with a synergist [10 μg piperonyl butoxide (PB) per insect]. Mortality was assessed after 24 and 48 hrs.

The following compounds were active at less than 5 μg/fly: 3,4.

C. Lethal Activity Against *Sitophilus granarius*

The activity of the compounds of the invention against *S. granarius* adults was demonstrated by addition of the compound in acetone solution to grain, to which the insects were later infected. Mortality was assessed after 6 days.

The following compound gave activity at less than 200 ppm solution of acetone: 2.

The following compound gave activity at least than 50 ppm solution of acetone: 1,3.

D. Lethal activity against *Culex quinquefasciatus*

The activity of the compounds of the invention against female Culex adults was demonstrated by direct spraying of 0.5 ml of compound in OPD/Methylene chloride. Mortality was assessed after 24 hours.

The following compounds were active at less than 1.0%: 1,2.

The following compounds were active at less than 0.1%: 3.

Formulations

| 1. Emulsifiable Concentrate | |
|---|---|
| Compound 1 | 10.00 |
| Ethylan KEO | 20.00 |
| Xylene | 67.50 |
| Butylated Hydroxyanisole | 2.50 |
| | 100.00 |
| 2. Wettable Powder | |
| Compound 1 | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |
| 3. Dust | |
| Compound 1 | 0.50 |
| Butylated Hydroxyanisole | 0.10 |
| Talc | 99.40 |
| | 100.00 |
| 4. Bait | |
| Compound 1 | 40.25 |
| Icing Sugar | 59.65 |
| Butylated hydroxy toluene | 0.10 |
| | 100.00 |
| 5. Lacquer | |
| Compound 1 | 2.5 |
| Resin | 5.0 |
| Butylated Hydroxy anisole | 0.5 |
| High aromatic white spirit | 92.0 |
| | 100.00 |
| 6. Aerosol | |
| Compound 1 | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound 1 | 0.1 |
| Butylated Hydroxy anisole | 0.1 |
| Xylene | 10.0 |
| Odourless Kerosene | 89.8 |
| | 100.00 |
| 8. Potentiated Spray | |
| Compound 1 | 0.1 |
| Piperonyl Butoxide | 0.5 |
| Butylated Hydroxyanisole | 0.1 |
| Xylene | 10.1 |
| Odourless Kerosene | 89.2 |
| | 100.0 |

SCHEME 1

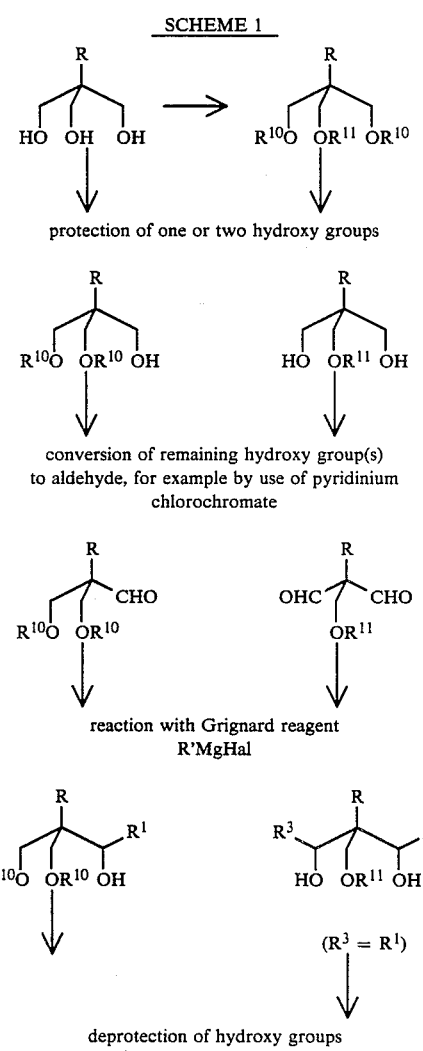

-continued
SCHEME 1

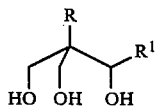 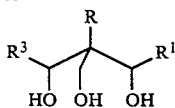

wherein $R^{10}$, $R^{11}$ are protecting groups that may be removed under different conditions, e.g. by hydrogenolysis and acid hydrolysis. Conveniently both groups $R^{10}$ are linked to form an isopropylidene group and $R^{11}$ is benzyl.

We claim:

1. A compound of the formula (I):

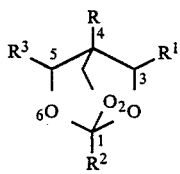

(I)

wherein R is $C_{2-10}$ alkyl, alkenyl or alkynyl, each optionally substituted by or methyl substituted by cyano, $C_{3-4}$ cycloalkyl, halo, $C_{1-4}$ alkoxy or a group $S(O)m R^4$ where $R^4$ is $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)m R^4$ as defined hereinbefore; $R^1$ is halo, $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms, a group $S(O)m R^4$ as defined hereinbefore or alkynyl substituted by tri-$C_{1-4}$ alkylsilyl, or $R^1$ is cyano, spirocyclopropyl, gem dimethyl, gem dicyano, gem diethynyl, oxo or methylene optionally substituted by cyano or $C_{1-3}$ alkyl optionally substituted by fluorine, or $R^1$ and R and the carbon atoms to which they are attached form a $C_{5-7}$ carbocyclic ring optionally substituted by halo, $C_{1-3}$ alkyl or alkoxy or $C_{2-3}$ alkenyl, $R^2$ is phenyl substituted by an $C_{2-3}$ alkynyl group or by a tri-$C_{1-4}$ alkylsilylalkynyl group and $R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo, or $R^3$ is cyano or halo.

2. A compound according to claim 1 in which R is n-propyl, n-butyl, i-butyl, s-butyl, t-butyl, cyclopentyl or cyclohexyl.

3. A compound according to claim 1 which $R^1$ is methyl, ethyl, trifluoromethyl, cyano or ethynyl.

4. A compound according to claim 1 in which $R^3$ is hydrogen or methyl.

5. A compound of the formula IA:

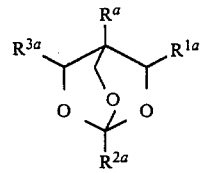

(IA)

wherein $R^a$ is $C_{2-4}$ alkyl, alkenyl or alkynyl, $C_{5-10}$ cycloalkyl or phenyl, each optionally substituted by cyano or $C_{1-4}$ alkoxy, $R^{1a}$ is cyano or $C_{1-3}$ alkyl, $C_{2-3}$ alkenyl or alkynyl each optionally substituted by cyano, $C_{1-4}$ alkoxy, $C_{1-4}$ alkylthio or halo, or $R^{1a}$ is cyano, gem dimethyl or $R^{1a}$ and $R^a$ and the carbon atoms to which they are attached form a $C_{5-7}$ carbocyclic ring optionally substituted by $C_{1-3}$ alkyl or alkoxy; $R^{2a}$ is phenyl, substituted by an $C_{2-3}$ alkynyl group and $R^{3a}$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo.

6. A compound selected from: 1-(4-ethynylphenyl)-3-methyl-4-n-propyl-2,6,7-trioxabicyclo[2,2,2]octane, 3-methyl-4-n-propyl-1-[4-(2-trimethylsilylethynyl)-phenyl]-2,6,7-trioxabicyclo-[2,2,2]octane, 1-(4-ethynylphenyl)-4-n-propyl-3-trifluoromethyl-2,6,7-trioxabicyclo[2,2,2]octane, 4-n-propyl-3-trifluoromethyl-1-[4-(2-trimethylsilylethynyl)-phenyl]-2,6,7-trioxabicyclo[2,2,2]octane, 3-cyano-1-(4-ethynylphenyl)-4-n-propyl-2,6,7-trioxabicyclo[2,2,2]octane, 4-t-butyl-3-cyano-1-(4-ethynylphenyl)-2,6,7-trioxabicyclo[2,2,2]octane, 4-t-butyl-3-cyano-1-[4-(2-trimethylsilylethynyl)-phenyl]-2,6,7-trioxabicyclo[2,2,2]octane, 4-n-Butyl-3-methyl-1-[4-(2-trimethylsilylethynyl)phenyl]-2,6,7-trioxabicyclo[2,2,2octane, 4-n-Butyl-1-(4-ethynylphenyl)-3-methyl-2,6,7-trioxabicyclo[2,2,2]octane, 3-Cyano-4-n-propyl-1-[4-(2-trimethylsilylethynyl)phenyl]-2,6,7-trioxabicyclo[2,2,2octane, 3-Cyano-1-(4-ethynylphenyl)-4-n-propyl-2,6,7-trioxabicyclo[2,2,2]octane.

7. An insecticidal or acaricidal composition comprising a compound of formula (I) in admixture with a carrier or diluent.

8. A synergized pesticidal composition comprising a compound of formula (I) together with a oxidase inhibitor or potentiator for the pesticidal compound of formula (I).

9. A method for the control of arthropod pests comprising the application to the pest or its environment of a compound of formula (I).

* * * * *